(12) United States Patent
Stubenrauch et al.

(10) Patent No.: US 9,488,662 B2
(45) Date of Patent: Nov. 8, 2016

(54) METHOD FOR THE DETECTION OF A MULTISPECIFIC BINDER

(71) Applicant: Hoffmann-La Roche Inc., Little Falls, NJ (US)

(72) Inventors: Kay-Gunnar Stubenrauch, Penzberg (DE); Markus Zadak, Sindelsdorf (DE)

(73) Assignee: Hoffmann-La Roche AG, Little Falls, NJ (US)

( * ) Notice: Subject to any disclaimer, the term of this patent is extended or adjusted under 35 U.S.C. 154(b) by 0 days.

(21) Appl. No.: 14/597,913

(22) Filed: Jan. 15, 2015

(65) Prior Publication Data

US 2015/0198608 A1 Jul. 16, 2015

Related U.S. Application Data

(63) Continuation of application No. PCT/EP2013/064683, filed on Jul. 11, 2013.

(30) Foreign Application Priority Data

Jul. 13, 2012 (EP) .................................... 12176342

(51) Int. Cl.
*G01N 33/68* (2006.01)
*G01N 33/543* (2006.01)

(52) U.S. Cl.
CPC .......... *G01N 33/686* (2013.01); *G01N 33/543* (2013.01)

(58) Field of Classification Search
None
See application file for complete search history.

(56) References Cited

U.S. PATENT DOCUMENTS

| | | | |
|---|---|---|---|
| 2014/0342382 | A1 | 11/2014 | Stubenrauch et al. |
| 2015/0072359 | A1 | 3/2015 | Stubenrauch et al. |

FOREIGN PATENT DOCUMENTS

| | | | |
|---|---|---|---|
| CN | 102207504 | A | 10/2011 |
| EP | 0 962 771 | A1 | 8/1999 |
| WO | 95/04931 | A1 | 2/1995 |
| WO | 01/36972 | A2 | 5/2001 |
| WO | 2006/096697 | A2 | 9/2006 |
| WO | 2008/060777 | A2 | 5/2008 |
| WO | 2008/119353 | | 10/2008 |
| WO | 2008/134046 | | 11/2008 |
| WO | 2010/040508 | A1 | 4/2010 |

OTHER PUBLICATIONS

CN102207504A English Abstract, pp. 1 ( Oct. 5, 2011).
Berkova et al., "Development of an Enzyme Immunoassay for the Measurement of Human Tumour Necrosis Factor-x (hTNF-x) Using Bispecific Antibodies to hTNF-x and Horseradish Peroxidase" Biotechnology and Applied Biochemistry 23(2):163-171 (Apr. 1, 1996).
Bruynck et al., "Characterisation of a humanised Bispecific Monoclonal Antibody for Cancer Therapy" British Journal of Cancer 67(3):436-440 (Mar. 1, 1993)
Chen et al., "Rapid Detection of Hepatitis B Virus Surface Antigen by an Agglutination Assay Meiated by a Bispecific Diabody Againt Both Human Erythrocytes and Hepatitis B Virus Surface Antigen" Clinical and Vaccine Immunology 14(6):720-725 (Apr. 18, 2007).
Doppalapudi et al., "Chemical Generation of Bisspecific Antibodies" PNAS 107(52):22611-22616 (Dec. 28, 2010).
Kemp, J.D. et al., "Inhibition of Lymphoma Growth in Vivo by Combined Treatment with Hydroxyethyl Starch Deferoxamine Conjugate and IgG Monoclonal Antibodies against the Transferrin Receptor" Cancer Research 55:3817-3824 ( 1995).
Mueller et al., "The first constant domain (CH1 and CL) of an antibody used as heterodimerization domain for bispecific miniantibodies" FEBS Lett. 422:259-264 ( 1998).
Porter et al., "An Electro-Active System of Immuno-Assay (EASI Assay) Utilising Self Assembled monolayer Modified Electrodes" Biosensors & Bioelectronics 16(9-12):875-885 (Dec. 1, 2001).
Reinartz et al., "Bispecific Multivalent Antibody Studies by Real-Time Interaction Analysis for the Development of an Antigen-Inhibittion Enzyme-Linked Immunosorbent Assay" Annlyst 121(6):767-771 (Jun. 1, 1996).
Rossi, E.A. et al., "Hexavalent bispecific antibodies represent a new class of anticancer therapeutics: 1. Properties of anti-CD20/CD22 antibodies in lymphoma" Blood 113(24):6161-6171 ( 2009).
Shapiro, R.I. et al., "Development and validation of immunoassays to quantify the half-antibody exchange of an IgG4 antibody, natalizumab (Tysabri) with endogenous IgG4" Journal of Pharmaceutical and Biomedical Analysis 55:168-175 ( 2011).
Wang, W. et al., "Identification of Natural Bispecific Antibodies against Cyclic Citrullinated Peptide and Immunoglobulin G in Rheumatoid Arthritis" PLOS One 6(1):e16527 ( 2011).
English translation of CN Office Action, pp. 1 from CN Appln. No. 201280063032.5.
European Search Report for Application No. EP11194350.
Guttikonda et al., "Monospecific and bispecific antibodies against *E. coli* O157 for diagnostics" Journal of Immunogical Methods 327:1-9 ( 2007).
Liu et al., "Bispecific monoclonal antibodies against a viral and an enzyme; utilities in ultrasensitive virus ELISA and phage display technology" Journal of Immunological Methods 274:115-127 ( 2003).
PCT Written Opinion of International Searching Authority for PCT/EP2012/075991.

*Primary Examiner* — Jacob Cheu
(74) *Attorney, Agent, or Firm* — Grant Kalinowski (57) ABSTRACT

Herein is reported a method for the detection of a multispecific antibody in a sample, whereby the multispecific antibody is specifically bound by i) a first anti-idiotypic antibody binding to a first binding specificity of the multispecific antibody, and ii) by a second anti-idiotypic antibody binding to a second binding specificity of the multispecific antibody and the formed complex is determined.

11 Claims, 4 Drawing Sheets

METHOD FOR THE DETECTION OF A MULTISPECIFIC BINDER

RELATED APPLICATIONS

This application is a continuation application of International Application No. PCT/EP2013/064683, filed Jul. 11, 2013, which claiming priority to application number EP12176342.9 filed Jul. 13, 2012, the contents of which are incorporated herein by reference.

The current invention is directed to a method for the detection of a multispecific binder in a sample, wherein the multispecific binder is detected using anti-idiotypic antibodies directed against the different binding specificities of the multispecific binder.

BACKGROUND OF THE INVENTION

Standard solid-phase immunoassays with antibodies involve the formation of a complex between an antibody adsorbed/immobilized on a solid phase (capture antibody), the antigen, and an antibody to another epitope of the antigen conjugated with an enzyme or detectable label (tracer antibody). In the assay, a sandwich is formed: solid phase/capture antibody/antigen/tracer antibody. In the reaction catalyzed by the sandwich among other things the activity of the antibody-conjugated enzyme is proportional to the antigen concentration in the incubation medium. Anti-idiotypic antibody assays are mentioned, for example, in U.S. Pat. No. 5,219,730; WO 87/002778; EP 0 139 389; and EP 0 170 302. Wadhwa, M., et al. (J. Immunol. Methods 278 (2003) 1-17) report strategies for the detection, measurement and characterization of unwanted antibodies induced by therapeutic biologicals. A method for producing anti idiotypic antibodies is reported in EP 1 917 854.

In WO 2008/119353 bispecific antibodies and methods for producing thereof are reported. Methods for determining the bivalency of protein and antibody therapeutics are reported in WO 2006/096697. In WO 2008/134046 potent, stable and non-immunosuppressive anti-CD4 antibodies are reported. Muller, K. M., et al. report that the first constant domain (CH1 and CL) of an antibody can be used as heterodimerization domain for bispecific miniantibodies.

SUMMARY OF THE INVENTION

It has been found that by using two anti-idiotypic antibodies as capture and as tracer antibody in a sandwich immunoassay for the determination of the amount of a multispecific antibody in a sample, whereby each of the anti-idiotypic antibodies binds to a different binding specificity of the multispecific antibody, influences due to the sample matrix (e.g. serum or human plasma, antigens, etc.) can be minimized. Additionally it is possible to use an assay setup that is more sensitive, less influencable by the sample matrix, can be performed faster, requires minimal removal/ dilution of sample matrix, and provides more flexibility for labeling/derivatization/immobilization of capture and/or tracer antibody, respectively. This is achieved by using two anti-idiotypic antibodies, one directed against the first binding specificity of the bispecific antibody and one against the second binding specificity of the bispecific antibody.

Thus, herein is reported a method for the (immunological) determination of the amount of a multispecific binder in a sample comprising the step of:

determining the amount of a complex formed between
   i) an anti-idiotypic antibody that specifically binds to a first binding specificity of the multispecific binder, and
   ii) the multispecific binder
by incubating the complex with an anti-idiotypic antibody that specifically binds to a second binding specificity of the multispecific binder, which is different from the first binding specificity of the multispecific antibody, and thereby determining the amount of the multispecific binder in the sample.

In one embodiment the anti-idiotypic antibody that specifically binds to a first binding specificity of the multispecific binder is conjugated to a solid phase.

In one embodiment the anti-idiotypic antibody that specifically binds to a second binding specificity of the multispecific binder is conjugated to a detectable label.

In one embodiment the sample comprises (human) serum or (human) plasma, and/or is a cell lysate, and/or comprises one or more antigens of the multispecific binder. In one embodiment the sample is (human) serum or (human) plasma.

In one embodiment the multispecific binder is selected from an antibody, a fusion polypeptide comprising an antibody or antibody fragment and a non-antibody polypeptide, a fusion polypeptide comprising an antibody or antibody fragment and a soluble receptor, or a fusion polypeptide comprising an antibody or antibody fragment and a peptidic binding molecule.

In one embodiment the multispecific binder is an antibody. In one embodiment the antibody is a bispecific antibody, or a trispecific antibody, or a tetraspecific antibody, or a pentaspecific antibody, or a hexaspecific antibody. In one embodiment the antibody is a bispecific antibody.

In one embodiment the binding specificity is a binding site or a pair of an antibody heavy chain variable domain and an antibody light chain variable domain.

In one embodiment the anti-idiotypic antibody that specifically binds to a first binding specificity of the multispecific binder is biotinylated and the solid phase is streptavidin coated. In one embodiment the solid phase is a streptavidin coated paramagnetic bead or a streptavidin coated sepharose bead.

In one embodiment the anti-idiotypic antibody that specifically binds to the second binding specificity of the multispecific binder is digoxigenylated.

In one embodiment the method comprises the step of determining the amount of a complex formed between
   i) an anti-idiotypic antibody that specifically binds to a first binding specificity of the multispecific binder,
   ii) the multispecific binder, and
   iii) an anti-idiotypic antibody that specifically binds to a second binding specificity of the multispecific binder and that comprises a detectable label,
by determination the detectable label in the formed complex.

In one embodiment the conjugation of an anti-idiotypic antibody to its conjugation partner is performed by chemically binding via N-terminal and/or $\epsilon$-amino groups (lysine), $\epsilon$-amino groups of different lysins, carboxy-, sulfhydryl-, hydroxyl- and/or phenolic functional groups of the amino acid backbone of the drug antibody and/or sugar alcohol groups of the carbohydrate structure of the drug antibody.

In one embodiment the anti-idiotypic antibody is a mixture comprising the anti-idiotypic antibody conjugated via at least two different amino groups to the solid phase. Such coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the antibody is conjugated to the solid phase via remaining free amino groups, i.e. the antibody obtained is conjugated to the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the anti-idiotypic antibody is conjugated to the solid phase by passive adsorption. Passive adsorption is, e.g., described by Butler, J. E., in "Solid Phases in Immunoassay" (1996) 205-225 and Diamandis, E. P., and Christopoulos, T. K. (Editors), in "Immunoassays" (1996) Academic Press (San Diego).

In one embodiment the anti-idiotypic antibody is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996), lectin/polysaccharide, steroid/steroid binding protein, hormone/hormone receptor, enzyme/substrate, IgG/Protein A and/or G, etc. In one embodiment the anti-idiotypic antibody is conjugated to biotin and immobilization is performed via immobilized avidin or streptavidin.

DETAILED DESCRIPTION OF THE INVENTION

Herein is reported an in vitro method for the determination of the amount of a multispecific binder, such as bispecific antibodies/drugs, in pre-clinical and clinical samples.

It has been found that a multispecific binder in a sample has to be detected by using two anti-idiotypic antibodies that bind to different binding specificities of the multispecific binder in order to minimize influences by the sample matrix and to allow a greater degree of flexibility in setting up and performing the immunological determination of the amount of the multispecific binder in the sample.

In the following the method as reported herein is exemplified with a multispecific antibody as embodiment of a multispecific binder.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

In certain embodiments, the multispecific binder is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the same antigen. In one embodiment the second epitope on the same antigen is a non-overlapping epitope.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "free antigen" denotes the antigen that can be specifically bound by a binding specificity of an antibody but which is currently not bound to this binding specificity. In one embodiment the free antigen is a not-antibody bound antigen or a non-antibody complexed antigen.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A. et al., Sequences of Proteins of Immunological Interest, 5th ed. Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "anti-idiotypic antibody" denotes an antibody, which specifically binds to a binding specificity such as a binding site of a parent antibody, i.e. which is directed e.g. against an antigen binding site of a parent antibody. In one embodiment the anti-idiotypic antibody specifically binds to one or more of the CDRs of the parent antibody. In one embodiment the parent antibody is a therapeutic antibody. In one embodiment the parent antibody is a multispecific antibody. In one embodiment the parent antibody is a bispecific antibody.

Two epitopes are overlapping if a signal reduction of 50% or more, in one embodiment of 75% or more, is detected by a surface plasmon resonance (SPR) assay using the immobilized antibody and soluble antigen, or vice versa, with the epitope in question at a concentration of 20-50 nM and the antibody for which the epitope overlap has to be detected at a concentration of 100 nM. Alternatively a method can be used in which epitope overlap of two antibodies binding to the same antigen is determined with the help of a competitive test system. For this purpose, for example with the help of a cell-based enzyme immunoassay (ELISA) employing cells expressing recombinant antigen epitopes, it is tested if the antibody for which the epitope overlap has to be detected competes with the other antibody for the binding to the immobilized antigen. For this purpose, the immobilized antigen is incubated with the antibody in labeled form and an excess of the antibody for which the epitope overlap has to be determined. By detection of the bound labeling there can easily be ascertained the epitope overlap. If a signal reduction of more than 70%, in one embodiment of more than 80%, at the same concentration, or a displacement of more than 80%, in one embodiment of more than 90%, at higher concentrations, in one case with a $10^5$-fold excess of the antibody for which epitope overlap has to be determined, referred to the known antibody is determined then epitope identity or overlap is present and both antibodies bind to the same or an overlapping epitope on the same antigen.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain as proteins a number of reactive side chains for coupling to a binding partner, such as a surface, a protein, a polymer (e.g. PEG, cellulose or polystyrol), an enzyme, or a member of a binding pair. Chemical reactive groups of antibodies are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pp. 50-100.

One of the most common reactive groups of proteins is the aliphatic ε-amine of the amino acid lysine. In general, nearly all antibodies contain abundant lysine. Lysine amines are reasonably good nucleophiles above pH 8.0 ($pK_a$=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of proteins to form amide linkages. The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on proteins, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio)propionamido]hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in antibodies is the carboxylic acid. Proteins contain carboxylic acid groups at the C-terminal position and within the side chains of aspartic acid and glutamic acid. The relatively low reactivity of carboxylic acids in water usually makes it difficult to use these groups to selectively modify proteins and other biomolecules. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. In one embedment the sample is obtained from a monkey, especially a cynomolgus monkey, or a rabbit, or a mouse or rat. Such substances include, but are not limited to, in one embodiment whole blood, serum, or plasma from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemiluminescense are also in one embodiment signal-emitting groups, with particular preference being given to ruthenium chelates, e.g. a ruthenium $(bispyridyl)_3^{2+}$ chelate. Suitable ruthenium labeling groups are described, for example, in EP 0 580 979, WO 90/05301, WO 90/11511, and WO 92/14138.

The term "therapeutic multispecific binder" denotes a multispecific binder which is intended for use in a human being. In one embodiment the multispecific binder is a multispecific antibody. In one embodiment the multispecific antibody is a bispecific antibody. In one embodiment the multispecific or bispecific antibody is a monoclonal antibody. In one embodiment the multispecific antibody or bispecific antibody is a human or humanized monoclonal antibody.

The term "experimental animal" denotes any mammal including domestic and farm animals as well as higher primates, however, excluding humans. In one embodiment the method as reported herein is performed with a sample obtained from an experimental animal selected from the group comprising mouse, rat, rabbit, goat, sheep, dog, cat, and primates like lemurs, monkeys, marmosets, and apes. If the experimental animal is a lesser ape the closest relatives to mankind, the great apes, especially the group of chimpanzees, bonobos, gorillas and orangutans are excluded.

The term "total therapeutic multispecific binder" denotes any therapeutic multispecific binder present in a sample of an experimental animal irrespective of whether the therapeutic multispecific binder is active (i.e., still reactive with its one or more binding partners), inactive, and/or binding partner complexed.

The term "active therapeutic multispecific binder" denotes the therapeutic multispecific binder present in a sample of an experimental animal that still is capable of binding one or more of its binding partners.

The term "binding partner-complexed therapeutic multispecific binder" denotes the therapeutic multispecific binder present in a sample of an experimental animal in which at least one binding specificity specifically binds to its binding partner.

Herein is reported an immunological determination method for the determination of the amount of a multispecific binder in a sample.

The immunological determination is performed as bridging assay using a capture molecule, a tracer molecule, and a detection molecule.

The capture molecule is in one embodiment bound to a solid phase. The capture molecule can be any of a binding partner of the multispecific binder (e.g. one of the antigens of a bispecific antibody), a general complexing agent of the multispecific binder (e.g. an Fc-receptor in case of a full length antibody, or an anti-Fc-region antibody in case of a full length antibody), or a first partner of a binding pair if the multispecific binder is derivatized with the second partner of a binding pair, or an anti-idiotypic antibody that specifically binds to a binding specificity of the multispecific binder.

The tracer molecule can be any of a binding partner of the multispecific binder (e.g. one of the antigens of a bispecific antibody but if one antigen is used as capture molecule a different antigen has to be used as tracer molecule), a general complexing agent of the multispecific binder (e.g. an Fc-receptor in case of a full length antibody with the proviso that this molecule is not already used as capture molecule, or an anti-Fc-region antibody in case of a full length antibody with the proviso that this antibody binds to a different epitope if the same kind of antibody is also used as capture molecule), or a first partner of a binding pair if the multispecific binder is derivatized with the second partner of a binding pair (with the proviso that a different binding pair is used as that used to immobilized the capture molecule), or an anti-idiotypic antibody that specifically binds to a binding specificity of the multispecific binder (with the proviso that this binds to a different binding specificity that an anti-idiotypic antibody used as capture molecule).

It has now been found that for the determination of the amount of a multispecific binder in a sample it is advantageous to use an anti-idiotypic antibody as capture molecule and as tracer molecule whereby the anti-idiotypic antibodies bind to different binding specificities of the multispecific binder.

By using an anti-idiotypic antibody as capture molecule and as tracer molecule in the immunological determination of a multispecific antibody in a sample the method is i) more robust/experiences less interference with respect to substances in the sample matrix, ii) does require less sample dilution, iii) can be performed quicker, iv) is more flexible with respect to the labeling/derivatization/immobilization of capture and/or tracer antibody compared to a method using the antigens of the multispecific binder as capture and tracer molecule.

It has been found that the immunological determination of the amount of a multispecific binder in a sample, especially in a serum or human plasma containing sample obtained from an experimental animal, is strongly influenced by the sample matrix if the antigens of the multispecific binder are used as capture and tracer molecule.

If the sample is obtained from an experimental animal in which, e.g. a pharmacokinetic study is conducted, the sample will contain beside the multispecific binder also other closely related components derived from the experimental animal. For example if the sample is serum obtained from the blood of an experimental animal it will also contain one or more of the binding partners (e.g. soluble ligands of a receptor or shed receptor molecules) of the multispecific binder (e.g. the antigens of a multispecific antibody), immunoglobulins of different subclasses in an amount higher or lower than that of the multispecific binder, non-specific complexing molecules etc. These molecules can all interfere in an immunological determination method.

For example in case of a bispecific antibody the sample comprises beside the bispecific antibody also one or both of the antigens of the bispecific antibody. This results in the presence of a mixture of free bispecific antibody, bispecific antibody complexed with one antigen, bispecific antibody complexed with two antigens and each of the afore listed molecules non-specifically complexed with other serum or human plasma components. The free bispecific antibody can be detected with any possible combination of capture and tracer molecule as outlined above. The antigen complexed antibody can principally also be detected with any of the above combinations but the sensitivity of the method will be reduced as some of the bispecific antibody is withdrawn from the total amount of antibody present in the sample as the antigen-complexed antibody is in an equilibrium with the non-complexed form. The amount of the antigen-complexed antibody is highly variable and, thus, influences the assay also in highly variable way. This can be counteracted at least partly by using prolonged incubation times, which on the other hand slows down the assay performance.

It has now been found that the sensitivity of an immunological determination method of the amount of a bispecific antibody in a serum or plasma sample obtained from an experimental animal can be improved by using as capture molecule and as tracer molecule an anti-idiotypic antibody which specifically binds to the CDRs of the different binding specificities of the bispecific antibody. Likewise the required time for performing the determination can be reduced as among other things no prolonged incubation times are necessary in order to shift binding equilibrium. Additionally the required amount of capture molecule/density of the capture molecule on the solid surface can be reduced as the bispecific antibody can be captured irrespective of the complexation with antigen and, thus, less capture molecule is required.

One aspect as reported herein is a method for determining the amount or concentration of a therapeutic multispecific binder, in one embodiment a multispecific antibody, especially a bispecific antibody, in a sample obtained from an experimental animal comprising the following steps in the following order:

a) incubating a sample with a first anti-idiotypic antibody that specifically binds to a first binding specificity of the multispecific binder, b) incubating the sample with a second anti-idiotypic antibody that specifically binds to a second binding specificity of the multispecific binder, whereby the second binding specificity is different from the first binding specificity, and c) correlating the complex formed in step b) to the amount or concentration of the therapeutic multispecific binder.

In one embodiment the multispecific binder is a multispecific antibody.

In one embodiment the multispecific binder is a bispecific antibody.

In one embodiment the binding specificity is a pair of an antibody heavy chain variable domain with its cognate antibody light chain variable domain.

In one embodiment the binding partner of one or more binding specificities of the multispecific binder is an antigen. In one embodiment the antigen is selected independently of each for each binding specificity other from soluble antigens and membrane-bound antigens. In one embodiment the antigen is selected independently of each other for each binding specificity from receptor ligands and cell surface receptors.

In one embodiment the method is an immunoassay. In one embodiment the immunoassay is a sandwich immunoassay.

In one embodiment the conjugation of the multispecific binder to its conjugation partner is performed by chemically binding via N-terminal and/or $\epsilon$-amino groups (lysine), $\epsilon$-amino groups of different lysins, carboxy-, sulfhydryl-, hydroxyl- and/or phenolic functional groups of the amino acid backbone of the antibody and/or sugar alcohol groups of the carbohydrate structure of the antibody.

In one embodiment the capture anti-idiotypic antibody is immobilized via a specific binding pair. In one embodiment the capture anti-idiotypic antibody is conjugated to biotin and immobilization is performed via immobilized avidin or streptavidin.

In one embodiment the tracer anti-idiotypic antibody is conjugated to the detectable label via a specific binding pair. In one embodiment the tracer anti-idiotypic antibody is conjugated to digoxygenin and linking to the detectable label is performed via an antibody against digoxygenin.

In one embodiment the experimental animal is selected from the group comprising the members of the families of marmosets and tamarins, old world monkeys, dwarf and mouse lemurs, gibbons and lesser apes, true lemurs, as well as crossings thereof.

In one embodiment the therapeutic antibody is a human or a humanized antibody. In one embodiment the human or humanized antibody is a monoclonal antibody. In one embodiment the total therapeutic antibody is detected, in another the active therapeutic antibody is detected and in one embodiment the therapeutic antibody is detected which is bound to its antigen.

In one embodiment the anti-idiotypic antibody is conjugated to a paramagnetic bead.

In one embodiment the anti-idiotypic antibody is conjugated to a solid phase.

Various aspects connected to the application of a therapeutic multispecific binder in an experimental animal may have to be assessed during pre-clinical studies. In certain settings it may be relevant to analyze the total amount of therapeutic multispecific binder present in a sample, or it may be important to analyze certain fragments of a therapeutic multispecific binder in a sample, certain modifications of a therapeutic multispecific binder in a sample, the concentration of therapeutic multispecific binder in a sample bound to its one or more binding partners in the sample, or the fraction of therapeutic multispecific binder in a sample still capable of binding to one or more of its binding partners. In one embodiment the method as reported herein is for the detection of total therapeutic multispecific binder, or active therapeutic multispecific binder, or binding-partner complexed therapeutic multispecific binder, respectively.

Total, active, or binding partner-complexed therapeutic multispecific binder can be detected directly in a method as reported herein.

In addition, it is also possible to indirectly assess any "inactive" therapeutic multispecific binder. Such inactive therapeutic multispecific binder may be for example a therapeutic bispecific antibody bound to one or both of its antigen, or a therapeutic bispecific antibody bound to a cross-reactive antigen, or a therapeutic bispecific antibody blocked by an auto antibody against the therapeutic bispecific antibody. In case the total multispecific binder amounts to more than the sum of active multispecific binder and binding partner-complexed multispecific binder, an additional fraction of multispecific binder comprising the inactive multispecific binder not bound to its corresponding binding partner will be present.

Various assay systems are at hand to analyze e.g., total, active or binding partner-complexed therapeutic multispecific binder.

Total multispecific binder for example can be detected in a so-called competitive immunoassay system or in a so-called sandwich type assay system.

Such assay may be performed without washing steps (homogeneous immunoassay) or with washing steps (heterogeneous immunoassay).

In one embodiment the amount of total therapeutic multispecific binder is detected in a sandwich type immunoassay, wherein an anti-idiotypic antibody is used at both sides of such sandwich assay, whereby the two anti-idiotypic antibodies specifically bind to different binding specificities of the multispecific binder. The anti-idiotypic antibody used at one side of such sandwich is bound or capable of binding to a solid phase (often referred to as capture anti-idiotypic antibody), whereas the anti-idiotypic antibody at the other side of such sandwich is labeled in such a manner that direct or indirect detection is facilitated (so-called tracer anti-idiotypic antibody). The amount of tracer anti-idiotypic antibody bound in such sandwich assay procedure is directly correlated to the amount of therapeutic multispecific binder in the sample investigated.

In the art (e.g. US 2003/0068664) assay systems are known, which allow for the detection of active therapeutic antibodies. Such systems require the binding of the antigen to a solid phase, binding of the therapeutic antibody to this bound antigen and detection of the therapeutic antibody bound via the antigen to the solid phase.

Detection of active multispecific binder in a sample may be achieved by convenient state of the art procedures. However, the detection of total therapeutic multispecific binder or of the fraction of therapeutic multispecific binder complexed with its binding partner is rather complicated and requires quite different assay set-ups and especially requires tailor-made reagents for each of the different assays. With the method as reported herein it is possible to assess the fraction of active therapeutic multispecific binder, total therapeutic multispecific binder, or binding partner-complexed therapeutic multispecific binder in test systems which are analogues to each other. By its very nature this kind of comparative assessment of total, active, or binding partner-complexed therapeutic multispecific binder should have advantages once quantitative comparisons are made in between these various fractions of therapeutic multispecific binder.

In one embodiment a sandwich type assay format is set up to detect the active therapeutic multispecific binder. In one embodiment the anti-idiotypic antibody which is binding to one binding specificity of the therapeutic multispecific binder is used as a capture anti-idiotypic antibody and the detection side of such sandwich assay either makes use of an antigen, which is specifically bound by a respective other binding specificity of the multispecific binder, in a labeled form, or alternatively after binding of an antigen, which is specifically bound by a respective other binding specificity of the multispecific binder, makes use of a second antibody not binding to or competing with the epitope recognized by the therapeutic multispecific binder, wherein the second antibody is specifically detectable and/or is labeled in such a manner that direct or indirect detection is facilitated.

The binding partner-complexed therapeutic multispecific binder is in one embodiment detected in a sandwich type assay format using an anti-idiotypic antibody that specifically binds to one binding specificity of the multispecific binder as a capture anti-idiotypic antibody. In the detection a second antibody is used binding to the binding partner that is specifically bound by a different binding specificity of the multispecific binder at an epitope which does not compete with the epitope of the therapeutic multispecific binder. Said second antibody in one embodiment is labeled in such a manner that direct or indirect detection is facilitated.

For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay), and radioisotopes. Metal chelates which can be detected by electrochemiluminescense are also in one embodiment signal-emitting groups used as detectable labels, with particular preference being given to ruthenium chelates. In one embodiment the labeling group is a ruthenium (bispyridyl)$_3^{2+}$ chelate.

Indirect detection systems comprise, for example, that the detection reagent, e.g., the tracer anti-idiotypic antibody is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. In one embodiment the first binding pair members comprise hapten, antigen and hormone. In one embodiment the haptens is selected from the group comprising digoxigenin, theophylline, carborane, and biotin as well as analogues thereof. The second partner of such binding pair, e.g. an antibody, streptavidin, etc., usually is labeled to allow for direct detection, e.g., by the labels as mentioned above.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates in "Practice and theory of enzyme immunoassays" (1990) 221-278, Eds. R. H. Burdon and v. P. H. Knippenberg, Elsevier, Amsterdam) and various volumes of "Methods in Enzymology", Eds. S. P. Colowick, N. O. Caplan and S. P., Academic Press), dealing with immunological detection methods, especially volumes 70, 73, 74, 84, 92 and 121.

In all the above immunological detection methods reagent conditions are chosen which allow for binding of the reagents employed, e.g. for binding of an antibody to its corresponding antigen. The skilled artisan refers to the result of such binding event by using the term complex. The complex formed in an assay method according to the present invention is correlated by state of the art procedures to the corresponding concentration of the therapeutic multispecific binder in the sample. Depending on the detection reagent employed this correlating step will result in the concentration of total, active or binding partner-complexed therapeutic multispecific binder.

Due to the use of one and the same reagent, the anti-idiotypic antibody in the different assays the values obtained can be easily compared to each other and even ratios thereof assessed. In one embodiment the present invention relates to the ratio of active to total therapeutic multispecific binder. This ratio may well serve as an indicator for the efficacy of a therapeutic multispecific binder.

Herein is reported in one aspect a method for the immunological determination of the amount of a multispecific binder in a sample comprising the step of:
  determining the amount of a complex formed between
    i) a first anti-idiotypic antibody that specifically binds to a first binding specificity of the multispecific binder, and
    ii) the multispecific binder
  by incubating the complex with a second anti-idiotypic antibody that specifically binds to a second binding specificity of the multispecific binder, which is different from the first binding specificity of the multispecific antibody, and thereby determining the amount of the multispecific binder in the sample.

In one embodiment the determination of the amount of the multispecific binder is by a bridging immunoassay. In one embodiment the immunoassay comprises a capture antibody and a tracer antibody, wherein the capture is conjugated to a solid phase, and the tracer antibody is conjugated to a detectable label. In one embodiment the capture antibody and the tracer antibody are both anti-idiotypic antibody that bind to different binding specificities of the multispecific binder.

In one embodiment the capture antibody are conjugated to a solid phase.

In one embodiment the tracer antibody comprises a detectable label.

The anti-idiotypic capture antibody useful in a method as reported herein can be conjugated to a solid phase. The conjugation is in one embodiment performed by chemical binding via N-terminal and/or ε-amino groups (lysine), ε-amino groups of different lysins, carboxy-, sulfhydryl-, hydroxyl- and/or phenolic functional groups of the amino acid backbone of the antibody and/or sugar alcohol groups of the carbohydrate structure of the antibody. The anti-idiotypic capture antibody is in one embodiment a mixture of at least two antibodies conjugated to a solid phase, wherein the at least two antibodies conjugated to a solid phase differ in the site at which they are conjugated to the solid phase. For example, the mixture of at least two antibodies conjugated to a solid phase may comprise an antibody conjugated via an amino acid of the amino acid backbone of the antibody to the solid phase and an antibody conjugated via a sugar alcohol group of a carbohydrate structure of the antibody to the solid phase. Also, for example, the mixture of at least two antibodies conjugated to a solid phase may comprise antibodies conjugated to the solid phase via different amino acid residues of their amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the antibody. In the latter case the amino acid can be of the same kind or of different kind The expression "differ in the antibody site" denotes a difference either in the kind of site, e.g. amino acid or sugar alcohol group, or in the number of the amino acid of the amino acid backbone, e.g. at which the antibody is conjugated to the solid phase. The same applies vice versa to the tracer antibody useful in a method as reported herein.

In one embodiment of the method the immunoassay comprises a capture antibody, a tracer antibody and a detection antibody, wherein the capture antibody is a biotinylated anti-idiotypic antibody that specifically binds to a first binding specificity of the multispecific binder conjugated to a solid phase via streptavidin, the tracer antibody is an anti-idiotypic antibody that specifically binds to a second binding specificity of the multispecific binder that is different from the first binding specificity conjugated to digoxygenin, and the detection antibody is an antibody against digoxygenin conjugated to horseradish peroxidase.

In one embodiment the method comprises the following steps:
incubating a sample comprising a multispecific binder with a first anti-idiotypic antibody that specifically binds to a first binding specificity of the multispecific binder, whereby a complex between the first anti-idiotypic antibody and the multispecific binder is formed,
incubating the complex between the anti-idiotypic capture antibody and the multispecific binder with a second anti-idiotypic antibody that specifically binds to a second binding specificity of the multispecific binder that is not identical, i.e. that is different, to the binding specificity to which the first anti-idiotypic antibody binds, whereby a complex between the first anti-idiotypic antibody, the multispecific binder, and the second anti-idiotypic antibody is formed, and
determining the amount of the complex formed in the previous step.

In one embodiment the determining the amount of the multispecific binder is by using a calibration curve.

In one embodiment the second anti-idiotypic antibody is conjugated to a detectable label.

In one embodiment the determining the amount of the multispecific binder is by determining the amount of immobilized detectable label.

In one embodiment the multispecific binder is a bispecific binder. In one embodiment the bispecific binder is a bispecific antibody.

The following examples and figure are provided to aid the understanding of the present invention, the true scope of which is set forth in the appended claims. It is understood that modifications can be made in the procedures set forth without departing from the spirit of the invention.

EXAMPLE

Example 1

General Method for the Determination of the Amount of a Bispecific Antibody in a Sample The concentrations of the multispecific binder/bispecific antibody was determined with an enzyme linked immunosorbent assay (ELISA)

For quantification of bispecific antibodies in mouse serum or plasma samples and eye lysates, a solid-phase serial sandwich immunoassay with biotinylated and digoxigenated monoclonal anti-idiotypic antibodies against the different binding specificities of the bispecific antibody as capture and detection antibodies was performed in order to verify the integrity of the bispecificity of the bispecific antibody. In this setup for a bispecific anti-VEGF/ANG2 antibody the biotinylated anti-idiotypic capture antibody specifically binds to the VEGF-binding site whereas the digoxigenated anti-idiotypic detection antibody specifically binds to the ANG2 binding site. The bound immune complex of capture antibody, bispecific antibody and detection antibody on the solid phase of the streptavidin coated micro titer plate (SA-MTP) was detected with a horseradish-peroxidase coupled to an anti-digoxigenin antibody. After washing unbound material from the SA-MTP and addition of ABTS-substrate, the gained signal was proportional to the amount of bispecific antibody bound on the solid phase of the SA-MTP. Quantification was done by converting the measured signals of the samples into concentrations referring to calibrators analyzed in parallel.

Setup for the Detection of a Bispecific Anti-VEGF/ANG2 Antibody

In a first step the SA-MTP is coated with 100 μl/well of the biotinylated anti-idiotypic capture antibody solution (anti-anti-VEGF antibody antibody M-2.45.51-Bi) with a concentration of 1 μg/ml for one hour at 500 rpm on a MTP-shaker. Meanwhile calibrators, QC-samples and samples were prepared. Calibrators and QC-samples were diluted to 2% serum matrix. Samples were diluted until the signals are within the linear range of the calibrators.

After coating the SA-MTP with anti-idiotypic capture antibody, the plate was washed three times with 300 µl/well washing buffer. Subsequently 100 µl/well of the calibrators, QC-samples and samples were pipetted on the SA-MTP and incubated for one hour at 500 rpm.

The bispecific anti-VEGF/ANG2 antibody was now bound with its VEGF binding site via the anti-idiotypic anti-VEGF antibody capture antibody to the solid phase of the SA-MTP. After incubation unbound analyte was removed by washing the plate. Thereafter 100 µl/well of the anti-idiotypic detection antibody (anti-anti-ANG2 antibody antibody M-2.6.81-Dig) with a concentration of 250 ng/ml was added to the wells of the SA-MTP. Afterwards, the plate was incubated for one hour at 500 rpm on a shaker. After washing, 100 µl/well of the second detection antibody (polyclonal anti-digoxigenin antibody-Fab-POD conjugate) at a concentration of 50 mU/ml was added to the wells of the SA-MTP and the plate was incubated for one hour at 500 rpm. After a final washing step to remove excess of second detection antibody, 100 µl/well substrate (ABTS) was added. The antibody-POD conjugate catalyzes the color reaction of the ABTS® substrate. The signal was then measured by an ELISA reader at 405 nm wavelength (reference wavelength: 490 nm ([405/490] nm)).

Example 2

Use of an Assay According to Example 1 for the Pharmacokinetic Characterization of a Bispecific Antibody in FcRn Mice Transgenic for Human FcRn In Life Phase The study included female C57BL/6J mice (background), which are mouse FcRn deficient and hemizygous transgenic for human FcRn (huFcRn, line 276-/tg).

Part 1

All mice were injected once intravitreally into the right eye with 2 µl/animal of the appropriate solution (i.e. 21 µg compound/animal (anti-VEGF/ANG2 antibody without the mutations I253A, H310A, and H435A (numbering according to EU Index of Kabat), see EP 12176299.1 for further details with respect to the used antibodies and amino acid sequences) or 23.6 µg compound/animal (anti-VEGF/ANG2 antibody comprising the mutations I253A, H310A, and H435A (numbering according to EU Index of Kabat)).

Mice were allocated to 2 groups with 6 animals each. Blood samples were taken from group 1 at 2, 24 and 96 hours and from group 2 at 7, 48 and 168 hours after application of the respective bispecific antibody.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 µl of the compound were injected using a 35-gauge needle.

Blood was collected via the retrobulbar venous plexus of the contralateral eye from each animal for the determination of the compound levels in serum.

Serum samples of at least 50 µl were obtained from blood after 1 hour at room temperature by centrifugation (9,300×g) at 4° C. for 3 min. Serum samples were frozen directly after centrifugation and stored frozen at −80° C. until analysis.

Treated eyes of the animals of group 1 were isolated 96 hours after treatment and of treated eyes of the animals of group 2 were isolated 168 hours after treatment.

Samples are stored frozen at −80° C. until analysis.

Part 2

All mice were injected once intravenously via the tail vein with 200 µl/animal of the appropriate solution (i.e. 21 µg compound/animal (anti-VEGF/ANG2 antibody without the mutations I253A, H310A, and H435A (numbering according to EU Index of Kabat)) or 23.6 µg compound/animal (anti-VEGF/ANG2 antibody comprising the mutations I253A, H310A, and H435A (numbering according to EU Index of Kabat)).

Mice were allocated to 2 groups with 5 animals each. Blood samples were taken from group 1 at 1, 24 and 96 hours and from group 2 at 7, 48 and 168 hours after application of the respective bispecific antibody.

Blood was collected via the retrobulbar venous plexus from each animal for the determination of the compound levels in serum.

Serum samples of at least 50 µl were obtained from blood after 1 hour at room temperature by centrifugation (9,300×g) at 4° C. for 3 min. Serum samples were frozen directly after centrifugation and stored frozen at −80° C. until analysis.

Preparation of Whole Eye Lysates (Mice)

The eye lysates were gained by physico-chemical disintegration of the whole eye from laboratory animals. For mechanical disruption, each eye was transferred into a 1.5 ml micro vial with conical bottom. After freeze and thawing, the eyes were washed with 1 ml cell washing buffer once (Bio-Rad, Bio-Plex Cell Lysis Kit, Cat. No. 171-304011). In the following step, 500 µl of freshly prepared cell lysis buffer was added and the eyes were grinded using a 1.5 ml tissue grinding pestle (Kimble Chase, 1.5 ml pestle, Art. No. 749521-1500). The mixture was then frozen and thawed five times and grinded again. To separate lysate from remaining tissue the samples were centrifuged for 4 min. at 4,500 g. After centrifuging the supernatant was collected and stored at −20° C. until further analysis in the quantification ELISA.

Analysis

The determination of the amount of bispecific antibody in the sample was performed according to Example 1.

Pharmacokinetic Evaluation

The pharmacokinetic parameters were calculated by non-compartmental analysis, using the pharmacokinetic evaluation program WinNonlin™ (Pharsight), version 5.2.1.

Results

A) Serum Concentrations

Results for serum concentrations are shown in Tables 1 to 2.

TABLE 1

Comparison of serum concentrations after intravitreal and intravenous application of anti-VEGF/ANG2 antibody without the mutations I253A, H310A, and H435A.

| ID | serum concentration after intravitreal application average concentration [µg/ml] | serum concentration after intravenous application average concentration [µg/ml] |
|---|---|---|
| 1 h | | 17.7 |
| 2 h | 9.8 | |
| 7 h | 10.4 | 12.1 |
| 24 h | 6.4 | 8.3 |

TABLE 1-continued

Comparison of serum concentrations after intravitreal and intravenous application of anti-VEGF/ANG2 antibody without the mutations I253A, H310A, and H435A.

| ID | serum concentration after intravitreal application average concentration [μg/ml] | serum concentration after intravenous application average concentration [μg/ml] |
|---|---|---|
| 48 h | 6.5 | 6.9 |
| 96 h | 3.4 | 4.1 |
| 168 h | 2.9 | 2.7 |

TABLE 2

Comparison of serum concentrations after intravitreal and intravenous application of anti-VEGF/ANG2 antibody with the mutations I253A, H310A, and H435A.

| ID | serum concentration after intravitreal application average concentration [μg/ml] | serum concentration after intravenous application average concentration [μg/ml] |
|---|---|---|
| 1 h |  | 18.4 |
| 2 h | 7.0 |  |
| 7 h | 8.7 | 10.0 |
| 24 h | 2.2 | 3.3 |
| 48 h | 1.0 | 1.0 |
| 96 h | 0.1 | 0.1 |
| 168 h | 0.0 | 0.0 |

B) Concentrations in Eye-Lysates of Left and Right Eyes

Results for concentrations in eye lysates are shown in Tables 3 to 4.

TABLE 3a

Concentrations of anti-VEGF/ANG2 antibody without the mutations I253A, H310A, and H435A in eye lysates after intravitreal application into right eye. mean concentration values from n = 6 mice

| ID | | mean concentration [ng/ml] |
|---|---|---|
| 96 h | left eye | 8.7 |
|  | right eye | 46.1 |
| 168 h | left eye | 4.3 |
|  | right eye | 12.9 |

TABLE 3b

Concentrations of anti-VEGF/ANG2 antibody without the mutations I253A, H310A, and H435A in eye lysates after intravenous application. mean concentration values from n = 5 mice

| ID | | mean concentration [ng/ml] |
|---|---|---|
| 96 h | left eye | 4.2 |
|  | right eye | 7.5 |
| 168 h | left eye | 3.4 |
|  | right eye | 6.1 |

TABLE 4a

Concentrations of anti-VEGF/ANG2 antibody with the mutations I253A, H310A, and H435A in eye lysates after intravitreal application into right eye. mean concentration values from n = 5 mice

| ID | | mean concentration [ng/ml] |
|---|---|---|
| 96 h | left eye | 0.3 |
|  | right eye | 34.5 |
| 168 h | left eye | 0.1 |
|  | right eye | 9.0 |

TABLE 4b

Concentrations of anti-VEGF/ANG2 antibody with the mutations I253A, H310A, and H435A in eye lysates after intravenous application. mean concentration values from n = 5 mice

| ID | | mean concentration [ng/ml] |
|---|---|---|
| 96 h | left eye | 0.0 |
|  | right eye | 0.1 |
| 168 h | left eye | 0.0 |
|  | right eye | 0.1 |

Example 3

Assay for the Pharmacokinetic Characterization of Bispecific Antibodies

The same set of samples comprising an anti-VEGF/ANG2 antibody in 10% human EDTA/plasma were analyzed with an antigen-based ELISA (A) and an anti-idiotypic antibody-based ELISA (B).

Figure 1:
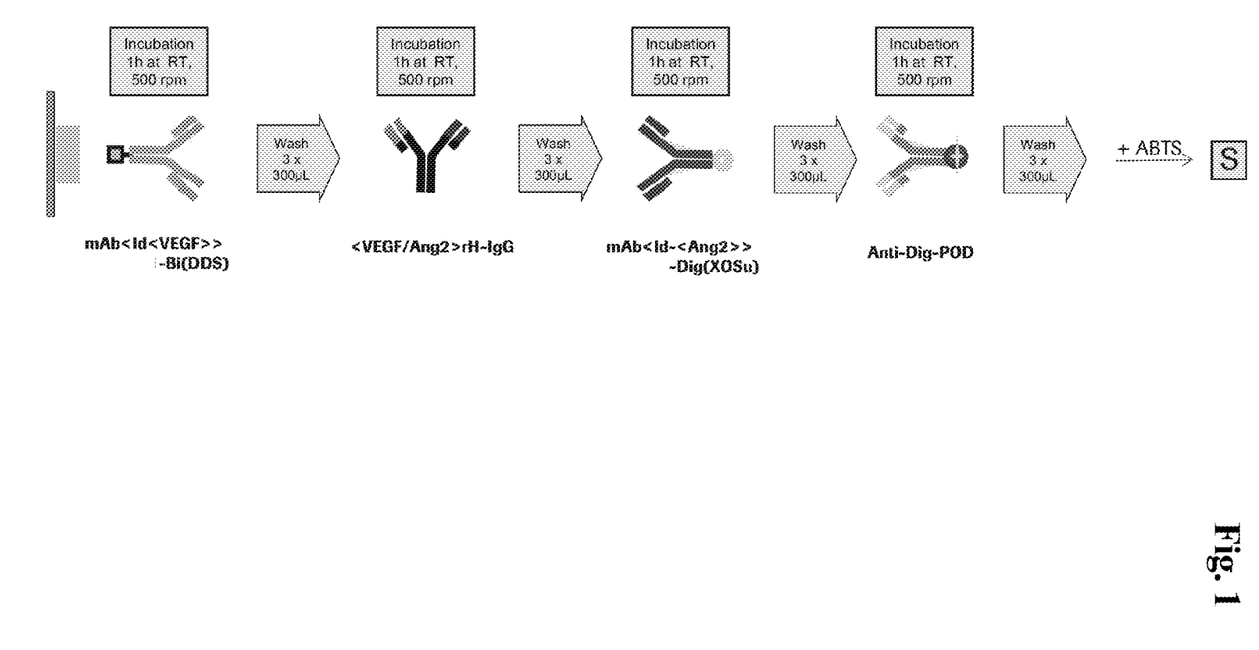
FIG. 1 Schematic pharmacokinetic ELISA assay principle for determination of concentrations of bispecific antibodies in serum and cell samples (anti-idiotypic antibody based ELISA).
Figure 2:
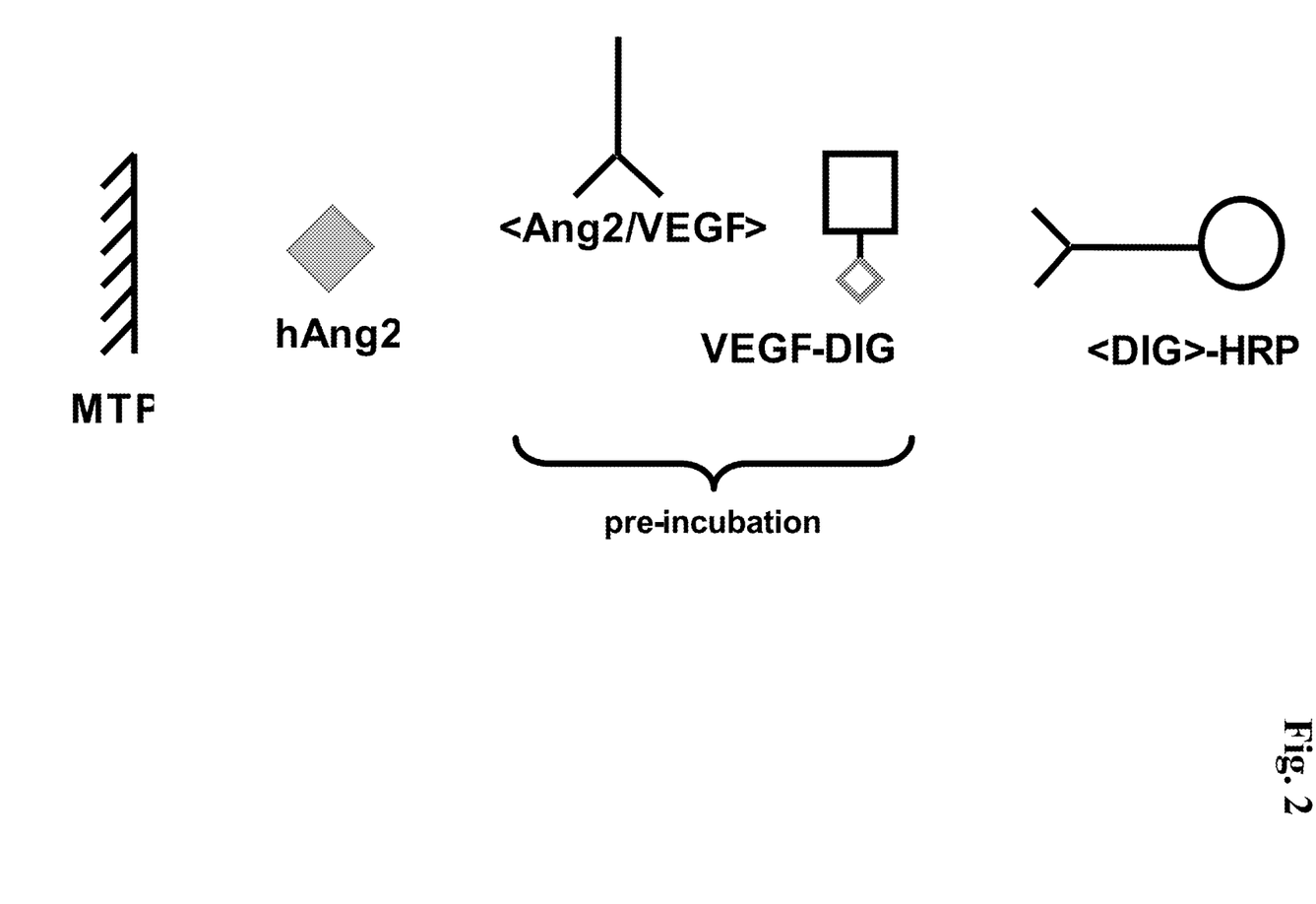
FIG. 2 Antigen-based sandwich ELISA for detection of anti-VEGF/ANG2 antibodies. Recombinant human angiopoietin 2 was directly coated to a micro titer plate. In parallel, samples containing anti-VEGF/ANG2 antibodies were pre-incubated with digoxigenin-labeled recombinant VEGF. After coating, the plate was washed and incubated with the pre-incubated mixture. The complexes of anti-VEGF/ANG2 antibody and digoxigenin-labeled VEGF bind to the ANG2 on the micro titer plate surface. Bound digoxigenin-labeled VEGF was detected with anti-digoxigenin antibody-HRP conjugate and ABTS.

Antigen-Based ELISA for Detection of Anti-VEGF/ANG2 Antibody:

Recombinant human angiopoietin 2 (ANG2) was directly coated to a Maxisorb micro titer plate for one hour, in the first step. In parallel, digoxigenin-labeled recombinant human VEGF was pre-incubated with the samples containing unknown amounts of anti-VEGF/ANG2 antibody or reference standards, respectively. Samples were diluted 10-fold prior to pre-incubation with digoxigenin-labeled VEGF. After coating and washing of the micro titer plate, the pre-incubated solution of anti-VEGF/ANG2 antibody and digoxigenin-labeled VEGF was pipetted to the micro titer plate and incubated for another hour. Anti-VEGF/ANG2 antibodies bound to digoxigenin-labeled VEGF from the pre-incubation solution were bound to immobilized ANG2. After another washing step, a polyclonal HRP-labeled (horseradish peroxidase-labeled) anti-digoxigenin antibody was added to the plate and incubated for another hour. Thereafter, the plate was washed and ABTS substrate solution was added to trigger a color reaction (see FIG. 2).

Anti-Idiotypic Antibody-Based ELISA for Detection of Anti-VEGF/ANG2 Antibody:

In a first step the SA-MTP (streptavidin-coated micro titer plate) was coated with biotinylated anti-idiotypic capture antibody solution (anti-anti-VEGF antibody antibody (M-2.45.51-BI)). Meanwhile calibrators, control-samples (QC-samples) and samples were prepared. Calibrators and QC-samples were diluted to 10% cynomolgus plasma matrix. Samples were diluted until the signals are within the linear range of the calibrators.

After coating the SA-MTP with anti-idiotypic capture antibody the plate was washed three times. Subsequently QC-samples and samples were pipetted on the SA-MTP and incubated for one hour at 500 rpm.

The bispecific anti-VEGF/ANG2 antibody was via its VEGF binding site to the anti-idiotypic anti-VEGF antibody capture antibody to the solid phase of the SA-MTP. After incubation unbound analyte was removed by washing the plate. Thereafter the anti-idiotypic detection antibody (anti-anti-ANG2 antibody antibody (M-2.6.81-DIG), 0.5 µg/ml) was added to the wells of the SA-MTP. Afterwards, the plate was incubated for one hour at 500 rpm on a shaker. After washing, the second detection antibody (polyclonal anti-digoxigenin antibody-Fab-POD conjugate (POD=peroxidase)) was added to the wells of the SA-MTP and the plate was incubated for one hour at 500 rpm. After a final washing step to remove excess of second detection antibody substrate (ABTS) was added. The antibody-POD conjugate catalyzes the color reaction of the ABTS® substrate. The signal was then measured by an ELISA reader at 405 nm wavelength (reference wavelength: 490 nm ([405/490] nm)). OD-Signals of calibration standards from 0.1-30 ng/ml in 10% human plasma were measured at 405 nm.

TABLE 5

Comparison of assay (A) and assay (B) for detection of anti-VEGF/ANG2 antibody.

| ng/mL | antigen-based assay | anti-idiotype antibody-based assay |
| --- | --- | --- |
| 30 | 0.963 | 2.282 |
| 15 | 0.296 | 1.982 |
| 7.5 | 0.117 | 1.493 |
| 3.75 | 0.077 | 0.930 |
| 1.88 | 0.037 | 0.506 |
| 0.94 | 0.036 | 0.292 |
| 0.47 | 0.032 | 0.169 |
| 0.23 | 0.031 | 0.098 |
| 0.12 | 0.030 | 0.065 |
| 0.06 | 0.030 | 0.047 |
| 0.03 | 0.030 | 0.037 |
| 0.01 | 0.030 | 0.032 |
| 0 | 0.030 | 0.033 |

Figure 3:
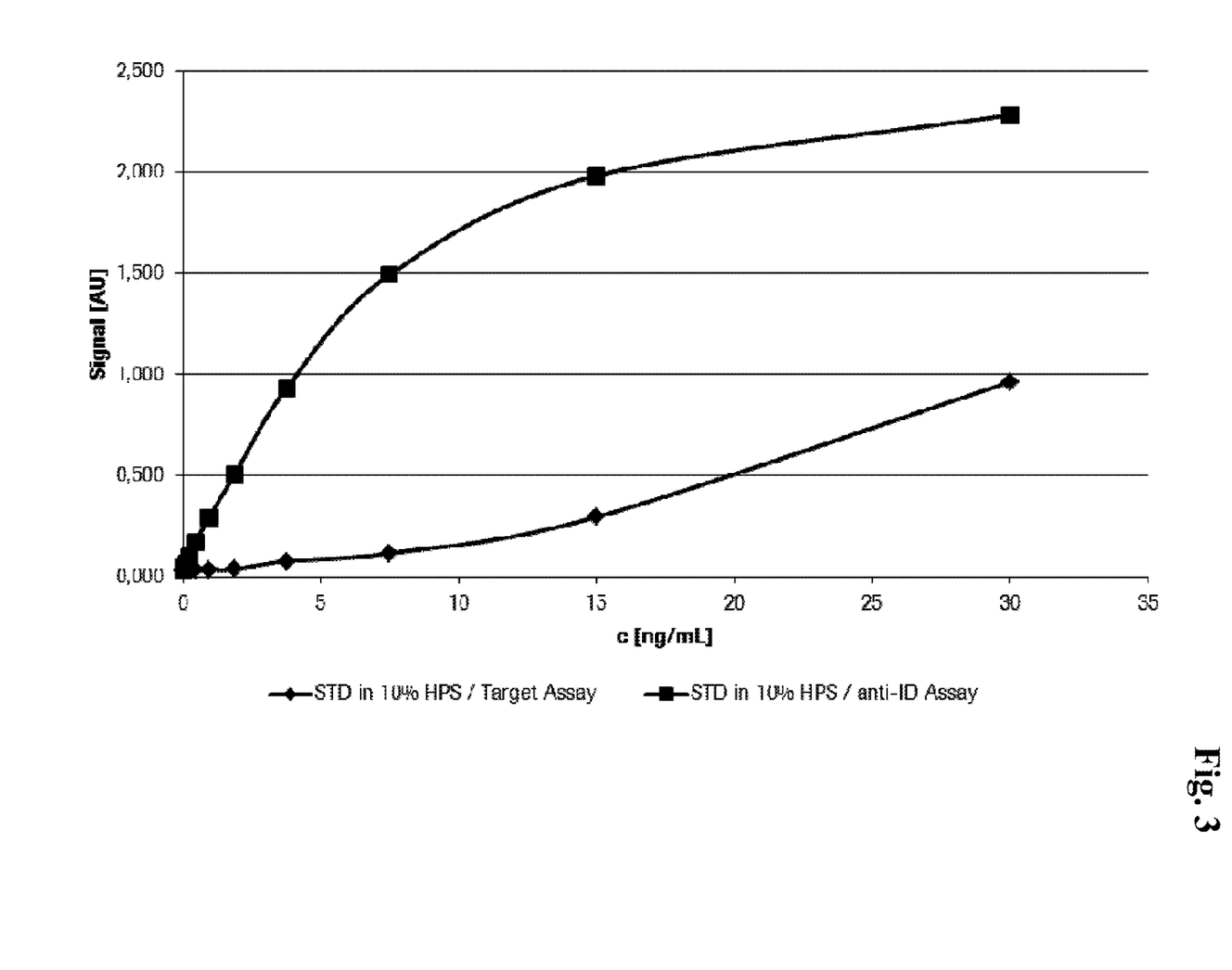
FIG. 3 Comparison of calibration curves obtained for antigen-based ELISA (A) and anti-idiotype antibody based ELISA (B) for detection of bispecific anti-VEGF/ANG2 antibody.

The calibration curves obtained with the different assays (A) and (B) are shown in FIG. 3.

Figure 4:
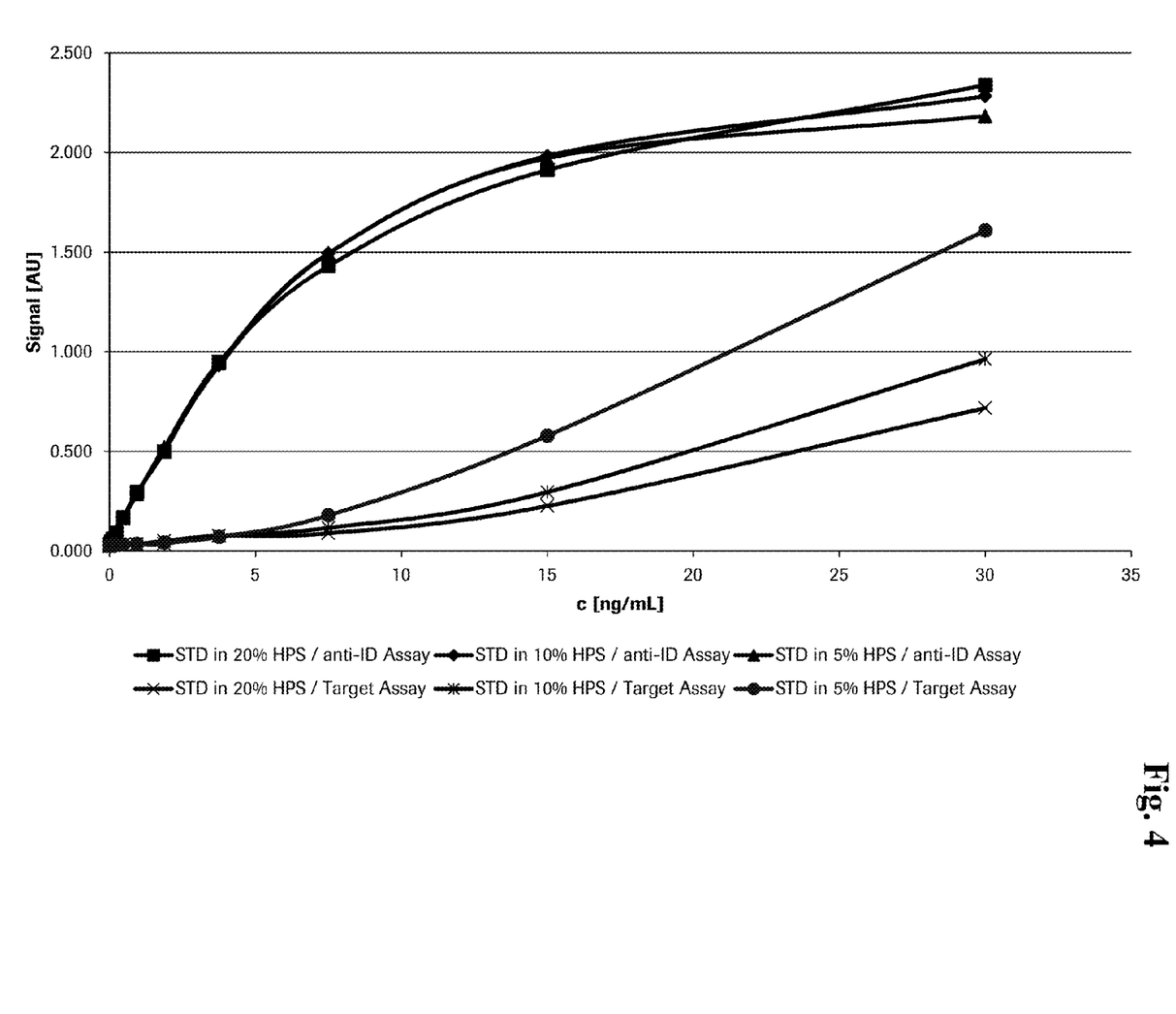
FIG. 4 Comparison of calibration curves of the anti-idiotype antibody based ELISA and the antigen-based ELISA in the presence of 5%, 10% and 20% human serum.

From FIG. 4 can be seen that the anti-idiotype antibody based assay provides comparable results in the presence of 5%, 10% and 20% human serum, whereas the antigen-based assay shows large deviations.

The invention claimed is:

1. A method for quantifying the amount of a multispecific antibody in a sample comprising:
   incubating a sample comprising a multispecific antibody with a first anti-idiotypic antibody that specifically binds to a first binding specificity of the multispecific antibody, whereby a complex between the first anti-idiotypic antibody and the multispecific antibody is formed,
   incubating the complex between the first anti-idiotypic antibody and the multispecific antibody with a second anti-idiotypic antibody that specifically binds to a second binding specificity of the multispecific antibody that is not identical to the binding specificity to which the first anti-idiotypic antibody binds, wherein the second anti-idiotypic antibody is conjugated to a first detectable label, whereby a complex between the first anti-idiotypic antibody, the multispecific antibody, and the second anti-idiotypic antibody is formed,
   contacting the complex between the first anti-idiotypic antibody, the multispecific antibody, and the second anti-idiotypic antibody with a detection antibody that is conjugated to a second detectable label and that specifically recognizes the first detectable label conjugated to the second anti-idiotypic antibody, and
   detecting the second detectable label in the complex formed with the detection antibody wherein the amount of the detection antibody that specifically binds to the first detectable label in the complex formed between the first anti-idiotypic antibody, the multispecific antibody, and the second anti-idiotypic antibody is directly correlated to the amount of multispecific antibody in the sample, thereby quantifying the amount of the multispecific antibody in a sample.

2. The method of claim 1, wherein the anti-idiotypic antibody that specifically binds to a first binding specificity of the multispecific antibody is conjugated to a solid phase.

3. The method of claim 2, wherein the first anti-idiotypic antibody that specifically binds to a first binding specificity of the multispecific antibody is biotinylated and the solid phase is streptavidin coated.

4. The method of claim 3, wherein the solid phase is a streptavidin coated paramagnetic bead or a streptavidin coated sepharose bead.

5. The method of claim 1, wherein the anti-idiotypic antibody that specifically binds to a first binding specificity of the multispecific antibody comprises a mixture of at least two antibodies conjugated to a solid phase, wherein the at least two antibodies conjugated to a solid phase differ in the site at which they are conjugated to the solid phase.

6. The method of claim 1, wherein the first detectable label is digoxygenin.

7. The method of claim 1, wherein the sample comprises at least one of serum, plasma, a cell lysate, and one or more antigens of the multispecific antibody.

8. The method of claim 7, wherein the sample is serum or plasma.

9. The method of claim 1, wherein the multispecific antibody is a bispecific antibody, a trispecific antibody, a tetraspecific antibody, a pentaspecific antibody, or a hexaspecific antibody.

10. The method of claim 9, wherein the multispecific antibody is a bispecific antibody.

11. The method of claim 10, wherein the bispecific antibody is a bispecific anti-VEGF/ANG2 antibody.

* * * * *